US011019422B2

(12) United States Patent
Pergament et al.

(10) Patent No.: US 11,019,422 B2
(45) Date of Patent: *May 25, 2021

(54) EARPHONES WITH ACTIVITY CONTROLLED OUTPUT

(71) Applicant: Samsung Electronics Co., Ltd., Suwon-si (KR)

(72) Inventors: Sammy Pergament, Stockholm (SE); Victor Påsse, Gothenburg (SE); Iman Habib, Gothenburg (SE); Jesper Johansson, Gothenburg (SE); Amir Adlouni, Värnamo (SE)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/928,576

(22) Filed: Jul. 14, 2020

(65) Prior Publication Data

US 2020/0344541 A1 Oct. 29, 2020

Related U.S. Application Data

(63) Continuation of application No. 16/416,480, filed on May 20, 2019, now Pat. No. 10,735,848, which is a (Continued)

(30) Foreign Application Priority Data

Nov. 21, 2014 (SE) .................................. 1451410-3

(51) Int. Cl.
*A61B 5/16* (2006.01)
*H04R 1/10* (2006.01)
(Continued)

(52) U.S. Cl.
CPC ......... *H04R 1/1041* (2013.01); *A61B 5/0205* (2013.01); *A61B 5/1118* (2013.01); (Continued)

(58) Field of Classification Search
CPC ...... H04R 1/1041; H04R 1/10; H04R 1/1025; A61B 5/6803; A61B 5/1118; (Continued)

(56) References Cited

U.S. PATENT DOCUMENTS

2004/0236236 A1 11/2004 Yanagidaira et al.
2006/0084551 A1 4/2006 Volpe
(Continued)

FOREIGN PATENT DOCUMENTS

EP 2777484 A2 9/2014
JP 2006-251376 A 9/2006
(Continued)

OTHER PUBLICATIONS

International Search Report and Written Opinion dated Feb. 18, 2016, in corresponding International Application No. PCT/SE2015/051220 (11 pages, in English).
(Continued)

*Primary Examiner* — Melur Ramakrishnaiah
(74) *Attorney, Agent, or Firm* — NSIP Law

(57) ABSTRACT

The present disclosure relates to an earphone apparatus and method. The earphone apparatus includes an earpiece, including a speaker, configured for arrangement relative to a user's ear for listening to audio from the speaker, a bio-sensor, a motion sensor, and a controller configured to determine an activity state of the user based on aggregated sensor data from the bio-sensor and the motion sensor over time, and to control audio output to the user based on the determined activity state.

36 Claims, 6 Drawing Sheets

Related U.S. Application Data continuation of application No. 15/990,698, filed on May 28, 2018, now Pat. No. 10,334,348, which is a continuation of application No. 15/597,717, filed on May 17, 2017, now Pat. No. 9,986,324, which is a continuation of application No. PCT/SE2015/051220, filed on Nov. 16, 2015.

(51) Int. Cl.

| *A61B 5/00* | (2006.01) |
|---|---|
| *A61B 5/0205* | (2006.01) |
| *A61B 5/11* | (2006.01) |
| *G06F 3/16* | (2006.01) |
| *A61B 5/024* | (2006.01) |

(52) U.S. Cl.
CPC ............ *A61B 5/165* (2013.01); *A61B 5/4809* (2013.01); *A61B 5/6803* (2013.01); *A61B 5/6815* (2013.01); *A61B 5/7225* (2013.01); *G06F 3/165* (2013.01); *H04R 1/1025* (2013.01); *A61B 5/02416* (2013.01); *A61B 2560/0209* (2013.01); *A61B 2562/0204* (2013.01); *A61B 2562/0219* (2013.01); *H04R 2201/107* (2013.01); *H04R 2430/01* (2013.01)

(58) Field of Classification Search
CPC ... A61B 5/0205; A61B 5/7225; A61B 5/2809; A61B 5/02416; A61B 2562/0219
USPC .......... 381/56, 71.6, 74, 104, 107, 310, 108, 381/370; 700/94
See application file for complete search history.

(56) References Cited

U.S. PATENT DOCUMENTS

| 2006/0107822 | A1 | 5/2006 | Bowen | |
|---|---|---|---|---|
| 2006/0155389 | A1* | 7/2006 | Pessolano | H04N 5/63 700/12 |
| 2007/0297618 | A1 | 12/2007 | Nurmi et al. | |
| 2008/0154098 | A1 | 6/2008 | Morris et al. | |
| 2008/0158000 | A1* | 7/2008 | Mattrazzo | H04M 1/6058 340/4.4 |
| 2009/0273478 | A1 | 11/2009 | Mei | |
| 2010/0303258 | A1 | 12/2010 | Pan | |
| 2011/0095875 | A1* | 4/2011 | Thyssen | G09G 5/10 340/407.1 |
| 2013/0106738 | A1* | 5/2013 | Kim | G08C 23/04 345/173 |
| 2013/0131519 | A1 | 5/2013 | LeBoeuf et al. | |
| 2013/0339859 | A1* | 12/2013 | Hardi | H04W 4/80 715/728 |
| 2013/0345842 | A1 | 12/2013 | Karakaya et al. | |
| 2014/0135076 | A1 | 5/2014 | Lee | |
| 2014/0135592 | A1 | 5/2014 | Ohnemus | |
| 2014/0169601 | A1 | 6/2014 | Pedersen | |
| 2014/0180039 | A1* | 6/2014 | LeBoeuf | A61B 5/4884 600/301 |
| 2014/0257535 | A1 | 9/2014 | Morris et al. | |
| 2014/0307878 | A1 | 10/2014 | Osborne et al. | |
| 2014/0318699 | A1 | 10/2014 | Longinotti-Buitoni et al. | |
| 2014/0334644 | A1 | 11/2014 | Selig et al. | |
| 2015/0078575 | A1* | 3/2015 | Selig | H04R 1/1025 381/74 |
| 2015/0281824 | A1 | 10/2015 | Nguyen et al. | |
| 2015/0339946 | A1* | 11/2015 | Pacione | A61B 5/165 434/236 |
| 2016/0089028 | A1 | 3/2016 | Chatterjee et al. | |
| 2016/0249133 | A1 | 8/2016 | Sorensen | |

FOREIGN PATENT DOCUMENTS

| WO | WO 2008/095167 A2 | 8/2008 |
|---|---|---|
| WO | WO 2015/051819 A1 | 4/2015 |

OTHER PUBLICATIONS

Nirjon et al., "MusicalHeart: A Hearty Way of Listening to Music", *Proceedings of the 10$^{th}$ ACM Conference on Embedded Network Sensor Systems*, Nov. 2012, pp. 1-14 (14 pages in English)

Chinese Office Action dated May 30, 2019 in corresponding Chinese Patent Application No. 201580063183.4 (19 pages in English, 11 pages in Chinese).

European Office Action dated Sep. 20, 2019 in European Patent Application No. 15 861 266.3. pp. 1-8 (8 pages in English).

Chinese Office Action dated Aug. 31, 2018 in Chinese Patent Application No. 201580063183.4 (4 page in English, 9 pages in Chinese).

* cited by examiner

EARPHONES WITH ACTIVITY CONTROLLED OUTPUT

CROSS-REFERENCE TO RELATED APPLICATION(S)

This application is a continuation of U.S. patent application Ser. No. 16/416,480, filed on May 20, 2019, which is a continuation of Ser. No. 15/990,698, filed on May 28, 2018, now U.S. Pat. No. 10,334,348, which is a continuation of U.S. patent application Ser. No. 15/597,717, filed May 17, 2017, now U.S. Pat. No. 9,986,324 issued on May 29, 2018, which is a continuation of International Application No. PCT/SE2015/051220 filed on Nov. 16, 2015, which claims the benefit under 35 USC § 119(a) of Swedish Patent Application No. 1451410-3, filed on Nov. 21, 2014, in the Swedish Patent and Registration Office, the entire disclosures of all of which are incorporated herein by reference for all purposes.

BACKGROUND

1. Field

The present application generally relates to the field of earphones, and in particular, earphones with an integrated sensor to control audio output.

2. Description of Related Art

Generally, within the technical field of earphones a user selects what he/she wants to listen to. It is common that users fall asleep when listening to music or other audio. In state of the art music players it is possible to set a timer for how long the music is going to play before stopping. However, this function requires that the user knows when he/she will fall asleep, or how soon the user expects to fall asleep. In many cases the user does not know how long time it will take to fall asleep; 5 minutes or 50 minutes, and therefore correctly setting a timer is not an easy task.

SUMMARY

In one general aspect, an earphone apparatus includes an earpiece, including a speaker, configured for arrangement relative to a user's ear for listening to audio from the speaker, a bio-sensor, a motion sensor, and a controller configured to determine an activity state of the user based on aggregated sensor data from the bio-sensor and the motion sensor over time, and to control audio output to the user based on the determined activity state.

The controller may be configured to determine the activity state of the user based on learned activity states of the user from the aggregated sensor data over time.

To determine the activity state of the user, the controller may determine a preliminary activity state of the user based on the sensor data from the bio-sensor, and confirm the preliminary activity state based on the sensor data from the motion sensor, to determine the activity state of the user.

The apparatus may further include a microphone, wherein the controller may be further configured to control the microphone to capture ambient sounds, and, to determine the activity state of the user, the controller may determine a preliminary activity state of the user based on the sensor data from the bio-sensor and the sensor data from the motion sensor, and confirm the preliminary activity state based on a determination whether the preliminary activity state of the user correlates to an activity state represented by the captured ambient sounds.

The bio-sensor and the controller may be configured within the earpiece, and the microphone may be connected to the earpiece or configured within the earpiece.

When the sensor data from the motion sensor and the sensor data from the bio-sensor indicate the user is resting, the controller may determine whether the activity state is a sleeping state trained based on aggregated detected movements over time by the motion sensor that are below a predetermined threshold, the trained sleeping state being updated over time.

The controller may determine where the sensor data of the motion sensor and the sensor data of the bio-sensor falls on a determined sleep-to-workout scale based on detected changes in movements of the user, to determine the activity state of the user.

The controller may be configured to determine between plural associated sub-states of the determined activity state based on detected changes in heart rate within a range of heart rates indicated by the sensor data of the bio-sensor and corresponding to the determined activity state, and selectively control the audio output based on the determination between the plural sub-states.

When the determined activity state is a workout state, the plural associated sub-states may include two or more of warming up, running, lifting weights, bicycling, climbing, dancing, jumping, doing yoga, and stretching sub-states.

The controller may consider between the plural associated sub-states of the determined activity state based on location information regarding a location of the user.

The controller and the bio-sensor may be configured within the earpiece and the controller may determine the location of the user.

The determination between the plural sub-states may be based on a determined progression between the plural sub-states.

The earpiece may be an in-ear earpiece or an out of ear earpiece, and the controller and at least one of the motion sensor and the bio-sensor may be configured within the earpiece.

The motion sensor and the bio-sensor may be configured in the earpiece.

The apparatus may further include a remote control unit including a second motion sensor, where the remote control unit is separate from the earpiece, and the controller may determine the activity state further based on sensor data from the second motion sensor.

The earpiece may be an in-ear earpiece or an out of ear earpiece, and the apparatus may further include another in-ear or out of ear earpiece that includes a corresponding speaker, the controller may be configured in the earpiece or the other earpiece, and the motion sensor and the bio-sensor may be both configured within one of the earpiece and the other earpiece or the motion sensor configured in the earpiece and the bio-sensor configured in the other earpiece, and the earpiece and/or the other earpiece may include a power harvesting component to perform a trickle energy capture to power the motion sensor and the bio-sensor.

The motion sensor may be an acceleration sensor and the bio-sensor is a heart rate sensor.

The earpiece may further include a communication module and wirelessly connects with a media player to obtain the audio output using the communication module.

The controller may be further configured to transmit control data to the media player, based on the determined activity state, for the controlling of the audio output based on the determined activity state.

The power harvesting component may harvest power from a wired connection, to the earpiece and/or the other earpiece, that provides audio to the earpiece and/or the other earpiece from a media player.

The controller may be further configured to selectively control respective periods of time the motion sensor and the bio-sensor are controlled to respectively measure motion and bio-signals, and the power harvesting component may selectively perform between the trickle energy capturing, with a storage of captured energy in a local power storage, during power off times of the bio-sensor of the respective periods of time and a supplying of the stored captured energy from the local power storage to the bio-sensor during power on times of the bio-sensor of the respective periods of time.

The motion sensor may be an acceleration sensor and the bio-sensor is a heart rate sensor, the earpiece may be an in-ear earpiece or an out of ear earpiece, and the apparatus may further include another in-ear or out of ear earpiece that that includes a corresponding speaker, with the motion sensor and the bio-sensor being both configured within one of the earpiece and the other earpiece or the motion sensor being configured in the earpiece and the bio-sensor being configured in the other earpiece.

The apparatus may further include a remote control unit including a second motion sensor, the remote control unit may be separate from the earpiece and the other earpiece, and the controller may determine the activity state further based on sensor data from the second motion sensor.

The controller may be further configured to filter the sensor data from the bio-sensor using the sensor data from the motion sensor and/or the sensor data from the second motion sensor.

The controller may be further configured to monitor the sensor data of the motion sensor and/or the sensor data from the second motion sensor for detected indications that the user is inputting a touch or tap command, and to not rely on, for the determining of the activity state of the user, the sensor data of the motion sensor and/or the sensor data from the second motion sensor that is determined to correspond to the detected indications that the user is inputting the touch or tap command.

The controller may be configured to determine whether the touch or tap is a command to control a pausing or resuming of audio output, to control a change in a song, genre, or playlist in the audio output, or to control an activation of a voice control.

The controller may be configured in the remote control unit, and the earpiece, the other earpiece, and the remote control unit are wiredly connected to each other.

The remote control unit may further include a power harvesting component to perform a trickle energy capture to power the motion sensor and the bio-sensor, the cable may be connected to a media player that provides the audio output, the controller may be further configured to selectively control respective periods of time the motion sensor and the bio-sensor are controlled to respectively measure motion and bio-signals, and the power harvesting component may selectively operate between the trickle energy capturing, with a storage of captured energy in a local power storage, during power off times of the bio-sensor of the respective periods of time and a supplying of the stored captured energy from the local power storage to the bio-sensor during power on times of the bio-sensor of the respective periods of time.

The controller and the bio-sensor may be configured within the earpiece, and the controller may be further configured to monitor the sensor data of the motion sensor for detected indications that the user is inputting a touch or tap command, and to not rely on, for the determining of the activity state of the user, the sensor data of the motion sensor that is determined to corresponds to the detected indications that the user is inputting the touch or tap command.

The motion sensor may be configured in the earpiece or another other earpiece of the earphone apparatus.

The controller may be configured to determine whether the touch or tap is a command to control a pausing or resuming of audio output, to control a change in a song, genre, or playlist in the audio output, or to control an activation of a voice control.

The earpiece may include an adjustable loop formed by a first attachment point of a cable and the earpiece and a second attachment point of the cable and the earpiece, the first attachment point and the second attachment point being configured so the adjustable loop selectively interacts with a concha of the user's ear to fixedly position the earpiece relative to the ear, and the cable may wiredly provide the audio output to the earpiece.

The earpiece may be an in-ear earpiece or an out of ear earpiece, the motion sensor and the bio-sensor may be configured within the earpiece, and the earpiece may include an adjustable loop formed by a first attachment point of a cable and the earpiece and a second attachment point of the cable and the earpiece.

The earpiece may be an in-ear earpiece or an out of ear earpiece, the apparatus may further include another in-ear or out of ear earpiece, the motion sensor and the bio-sensor may be both configured within one of the earpiece and the other earpiece or the motion sensor configured in the earpiece and the bio-sensor is configured in the other earpiece, and the earpiece may include an adjustable loop formed by a first attachment point of a cable and the earpiece and a second attachment point of the cable and the earpiece.

The cable may wiredly connect the earpiece to the other earpiece.

The controller may be further configured to determine an activity state transition between activity states of the user based on both the sensor data from the bio-sensor and the sensor data from the motion sensor to determine the activity state of the user.

The controller may be further configured to determine a preliminary activity state of the user based on the sensor data from the bio-sensor, to confirm the preliminary activity state based on the sensor data from the motion sensor to determine the activity state of the user.

To control the audio output, the controller may adjust the audio output to match a determined low activity when the determined activity state is a predetermined low activity state and adjust the audio output to match a determined high activity when the determined activity state is a predetermined high activity state.

The controlling of the audio output may include one of stopping, pausing, playing, increasing volume, decreasing volume, matching a beat per minute, a cadence, rhythm, predetermined user selection, genre, and predefined user playlist or specific track selection.

The controller may be further configured to obtain cadence sensor data from an external exercise equipment cadence sensor, and to determine the activity state further based on the obtained cadence sensor data.

The controller may be further configured to determine the activity state from among plural user preset activity states set through a user interface connected to the controller.

In one general aspect, an earphone method of an earphone apparatus having earpieces configured for respective arrangements relative to a user's ears for listening to audio includes controlling respective measuring of bio-signals and motion changes of a user by the earpieces, aggregating sensor data of the measured bio-signals and motion changes of the user over time, determine an activity state of the user based on the aggregated sensor data, and selectively controlling the audio output to the user based on the determined activity state.

The method may further include learning activity states of the user from the aggregated sensor data, and the determining the activity state may determine the activity state from among the learned activity states.

The learning of the activity states may include learning a sleeping state based on aggregated detected movements over time of the user that are below a predetermined threshold, and updating the learned sleeping state over time.

The determining of the activity state may include determining between plural associated sub-states of the determined activity state based on detected changes in heart rate within a range of heart rates indicated by the measured bio-signals and corresponding to the determined activity state, and the selective control of the audio output may be performed based on the determination between the plural sub-states.

Then the determined activity state is a workout state, the plural associated sub-states may include two or more of warming up, running, lifting weights, bicycling, climbing, dancing, jumping, doing yoga, and stretching sub-states.

The method may further include determining a location of the user, and the determining between the plural associated sub-states may include determining between the plural associated sub-states of the determined activity state based on the determined location of the user.

The determination between the plural sub-states may be based on a determined progression between the plural sub-states.

The determining of the activity state may be further based on sensor data from a motion sensor of a remote control unit separate from the earpieces.

The method may further include monitoring the measured motion changes for detected indications that the user is inputting a touch or tap command, and the determining of the activity state of the user may include not relying on, for the determining of the activity state of the user, the measured motion changes that are determined to correspond to the detected indications that the user is inputting the touch or tap command.

The monitoring of the measured motion changes may include determining whether the touch or tap is a command to control a pausing or resuming of the audio output, to control a change in a song, genre, or playlist in the audio output, or to control an activation of a voice control.

The method may further include performing a trickle energy capturing of energy to power a motion sensor and bio-sensor of the earpieces, which respectively perform the measuring of the bio-signals and the motion changes The trickle energy capturing of energy may include capturing trickle energy from a cable connected to at least one of the earpieces, the cable being connected to a media player that is separate from the earpieces and which provides the audio output.

The method may further include selectively controlling respective periods of time the motion sensor and the bio-sensor are controlled to respectively measure the motion changes and the bio-signals, and selectively performing between the trickle energy capturing, with a storage of captured energy in a local power storage, during power off times of the bio-sensor of the respective periods of time and a supplying of the stored captured energy from the local power storage to the bio-sensor during power on times of the bio-sensor of the respective periods of time.

The controlling of the audio output may be performed by transmitting control data by a controller included in one of the earpieces to a media player to control a providing of the audio output, the controller performing the determining of the activity state of the user.

The controlling of the audio output may include one of stopping, pausing, playing, increasing volume, decreasing volume, matching a beat per minute, a cadence, rhythm, predetermined user selection, genre, and predefined user playlist or specific track selection.

The method may further include obtaining cadence sensor data from an external exercise equipment cadence sensor, and the determining of the activity state may include determining the activity state further based on the obtained cadence sensor data and/or the controlling of the audio output is further based on the obtained cadence sensor data.

The method may further include providing a user interface to collect user defined preset activity state information, and the determining of the activity state may include determining the activity state from among plural preset activity states that are defined based on the preset activity state information.

In one general aspect, provided is a non-transitory computer readable medium storing instructions, which when implemented by a processor, cause the processor to implement one or more or all operations described herein.

In one general aspect, an earphone apparatus includes an earpiece, including a speaker, configured for arrangement relative to a user's ear for listening to audio from the speaker, a bio-sensor, a motion sensor, and a controller configured to determine an activity state transition between activity states of the user based on both sensor data from the bio-sensor and sensor data from the motion sensor, and to control audio output to the user based on the determined activity state transition.

When the activity state transition is a falling asleep state, as a transition between a resting state to a sleep state, the controller may control the audio output to the user to gradually decrease a volume of audio while the user is in the falling asleep state.

When the controller determines that an activity state of the user is a sleep state based on both the sensor data from the bio-sensor and the sensor data from the motion sensor, the controller may control the audio output to the user to cease.

The earpiece may be an in-ear earpiece or an out of ear earpiece, and the controller and at least one of the motion sensor and the bio-sensor may be configured within the earpiece.

The motion sensor and the bio-sensor may be configured in the earpiece.

The apparatus may further include a remote control unit including a second motion sensor, where the remote control unit may be separate from the earpiece, and the controller may determine the activity state transition further based on sensor data from the second motion sensor.

The earpiece may be an in-ear earpiece or an out of ear earpiece, and the apparatus may further include another in-ear or out of ear earpiece, and motion sensor and the bio-sensor may both be configured within one of the earpiece and the other earpiece or the motion sensor may be configured in the earpiece and the bio-sensor configured in the other earpiece.

The apparatus may further include a remote control unit including a second motion sensor, the remote control unit may be separate from the earpiece and the other earpiece and the controller may determine the activity state transition further based on sensor data from the second motion sensor.

The controller may be configured in the remote control unit.

The earpiece, the other earpiece, and the remote control unit may be wiredly connected through a same cable.

In one general aspect, an earphone apparatus includes an earpiece, including a speaker, configured for arrangement relative to a user's ear for listening to audio from the speaker, a bio-sensor, a motion sensor, and a controller configured to determine a preliminary activity state of the user based on the sensor data from the bio-sensor, to confirm the preliminary activity state based on the sensor data from the motion sensor to determine an activity state of the user, and to control audio output to the user based on the determined activity state.

Other features and aspects will be apparent from the following detailed description, the drawings, and the claims.

Figure 2:
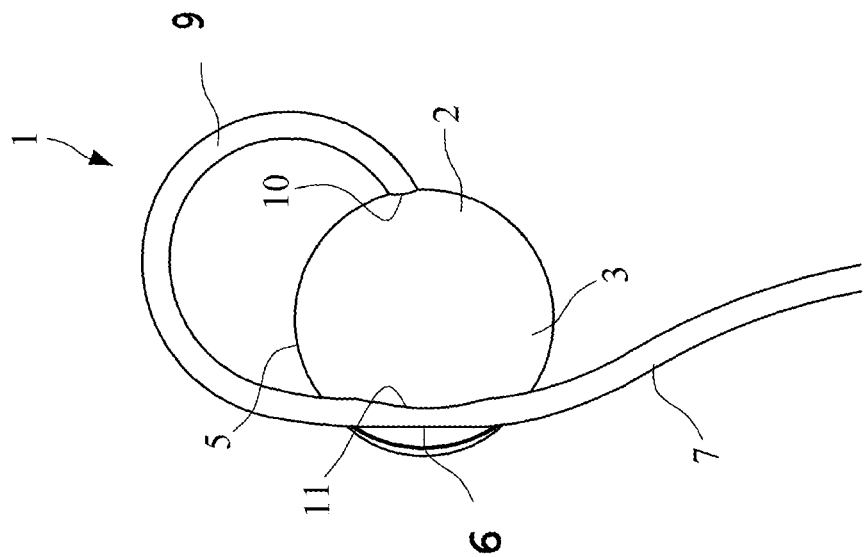
FIG. 2 illustrates a front view of an earphone according to one or more embodiments.

Throughout the drawings and the detailed description, unless otherwise described or provided, the same drawing reference numerals will be understood to refer to the same or like elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

The terminology used herein is for the purpose of describing particular examples only, and is not to be used to limit the disclosure. As used herein, the singular forms "a," "an," and "the" are intended to include the plural forms as well, unless the context clearly indicates otherwise. As used herein, the term "and/or" includes any one and any combination of any two or more of the associated listed items. As used herein, the terms "include," "comprise," and "have" specify the presence of stated features, numbers, operations, elements, components, and/or combinations thereof in at least one embodiment, such as when it is indicated that such stated features, numbers, operations, elements, components, and/or combinations thereof may be included in an example. However, the use of the terms "include," "comprise," and "have" in the Specification do not preclude the presence or addition of one or more other features, numbers, operations, elements, components, and/or combinations thereof in other embodiments, and do not preclude in the Specification the lack of presence of any of such features, numbers, operations, elements, components, and/or combinations thereof in still other embodiments unless explicitly or contextually/implicitly clearly explained otherwise.

In addition, terms such as first, second, A, B, (a), (b), and the like may be used herein to describe components. Each of these terminologies is not used to define an essence, order, or sequence of a corresponding component but used merely to distinguish the corresponding component from other component(s).

Throughout the specification, when an element, such as a layer, region, or substrate, is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there can be no other elements intervening therebetween. Likewise, expressions, for example, "between" and "immediately between" and "adjacent to" and "immediately adjacent to" may also be construed as described in the foregoing.

Unless otherwise defined, all terms, including technical and scientific terms, used herein have the same meaning as commonly understood by one of ordinary skill in the art to which this disclosure pertains consistent with and after an understanding of the present disclosure. Terms, such as those defined in commonly used dictionaries, are to be interpreted as having a meaning that is consistent with their meaning in the context of the relevant art and the present disclosure, and are not to be interpreted in an idealized or overly formal sense unless expressly so defined herein.

A function or an operation illustrated in a block may be performed not in a sequential order according to examples. For example, functions or operations illustrated in successive blocks may be actually performed concurrently, or an order of the blocks may be changed based on related functions or operations.

As described above, in the field of earphones, a user may set a sleep mode, which may control when audio output is scheduled to cease. However, the user will not know when sleep will begin, and often may not even set the sleep mode or may forget to set the sleep mode. Consequently, the user may set the timer with a too long time span, or may not activate the sleep timer at all, and may therefore accidently be woken from the audio output and/or waste battery resources of the player apparatus and the earphones while asleep.

Accordingly, it has been found that there is a desire for an improved earphone technology with an improved sleep function, as only an example. It has been found that a state of the user may be determined with higher accuracy when both of two different types of sensor data are considered to determine the state of the user, compared to previous approaches where a separate media player may determine what activity the user is currently performing based on sensed motion information or separately where a media player determines an activity level based on a sensed heart rate from a heart rate monitor.

For example, by considering both data from an example pulse rate detector and a motion sensor included in earphones worn by the user, the determination of a state of the user can be performed more accurately than previous approaches, as data from only one of the pulse rate detector and the motion sensor may be insufficient to determine a state of the user, e.g., for providing an appropriate and correct audio output. For example, a user's pulse may increase due to a state of nervousness or stress. However, if a controller of the earphone system determines the "workout-state" of the user based on the high pulse rate, and thereby selectively controls an increased tempo audio output, the audio output may not be desirable to the user since the fast beat music may only exacerbate the stress state of the user. Rather, by considering both data from the example pulse rate detector and the example motion sensor, a controller of an earphone system may correctly determine that a user has a high pulse that is not coincident with activity by the user or not generated by such user activity, and thus, may determine that the user is in a stressed state. In such an example, the controller may then, based on the determined stressed state, control or adjust audio output to be a calming or calmer lower speed beat relaxing music or preset relaxing sounds. This may be desirable for persons in psychological distress, for example.

As another example, earphones may be provided with an improved sleep function. In such an example, audio output may be controlled to be dependent on a user's determined state. For example, audio output may be controlled dependent on the user's determined state and corresponding predetermined and/or personalized audio output. The determinable states of the earphone system may be set by the user and/or be predetermined. Also, associated predetermined and/or personalized audio output operations may then be controlled based on the determined user's state. For example, select audio output operations may be differently performed dependent on whether the user's state is determined to be a sleeping, resting, running, working out, or other activity level dependent state, as only examples. The user's state is determined by a controller of the earphone system based on at least two different types of sensor data, such as measured first motion data and measured bio-signal type data. For example, the detected first motion data and detected bio-signal type data may be respectively captured by one or more first motion sensors and one or more bio-signal sensors included in one or more earpieces of the earphones. The user's state may be further determined based on additional measured data, such as based on captured audio type data, measured cadence or stride type data, and/or determined/measured location type data. The user's state may also be determined based on an additional detected second motion data, such as by a second motion sensor arranged in the earphone system distinct from the earphones of the earphone system. Still further, either or both of the example detected first or second motion data may be further considered or used to filter the detected bio-signal, such as to remove motion artifacts, e.g., prior to consideration of the bio-signal type data with the, for example, first motion data to determine the state of the user. A controller of the earphone system, such as included in either of the earpieces or a remote control unit in communication with the earpieces, may then selectively provide or adjust audio output to the user corresponding to the user's determined state.

In the following, while earphones may be described in relation to in-ear earphones, embodiments equally include on-ear earphones, headphones, and or a single earphone in, for example, a Bluetooth headset for a phone, any wired or wireless communication configuration from a mobile or stationary home audio equipment, as well as one or more wireless headsets and audio distribution system to be used during guided tours, theme parks, public gyms, as only non-limiting examples. Embodiments herein may additionally include examples where the earphone(s) are configured to interact with one or more central audio equipment available for multiple connections to earphones.

In addition, herein "audio output" should be understood as referring to any sound content that may be transmitted or generated from an audio source to a speaker unit of the earphones. The audio output includes but is not limited to music, relaxation sounds, speaking, pod casts, audio books etc. Moreover, herein "media player" should be understood as being any source from which audio output may be generated and/or transmitted, including but not limited to a smart phone, music player, DVD player, radio, TV, computer, tablet etc. Thus, herein, a media player herein may refer to a portable or mobile processing device and/or a stationary processing device, which can either or both generate and transmit audio. The media player may obtain the corresponding audio data or read the audio data from an internal memory of the media player. Alternatively, the controller of one or more of the earpieces or a remote control unit of the earphone system may be configured to perform the operations of the media player 13.

Figure 1:
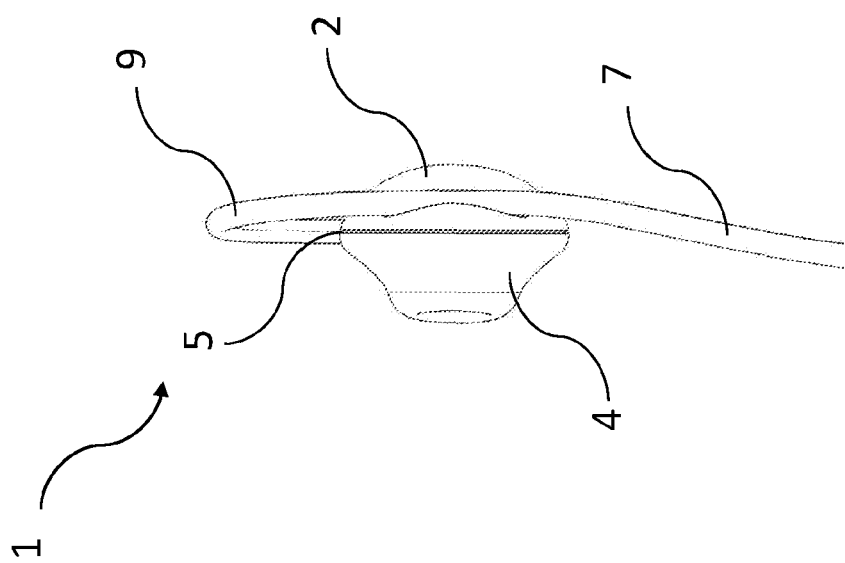
FIG. 1 illustrates a side view of an earphone according to one or more embodiments.

FIG. 1 illustrates a side view of an earphone according to one or more embodiments. Referring to FIG. 1, an earphone 1 may include an earpiece 2 that includes a front side portion 3 and an active side portion 4, for example. The earpiece 2 may further include a rim 5 arranged between the front side portion 3 and active side portion 4, for example.

The front side portion 3 and the active side portion 4 may be physically arranged to oppose each other, for example, and may joined together by the example rim 5.

In an example, the earpiece 2 may further include a recess 6. For example, the recess 6 may be configured so as to create a slot or crimping section across a portion of the earpiece 2. The recess 6 may be arranged on any of the front side portion 3, active side portion 4, and rim 5. For example, the recess 6 may be formed only on the front side portion 3, formed on the front side portion 3 and rim 5, formed on the front side portion 3, the rim 5, and the active side portion 4, formed on the rim 5 and the active side portion 4, or formed only on the active side portion 4. When formed on the front side portion 3 or active side portion 4 the recess 6 may be formed near the rim 5, though embodiments are not limited thereto. In an example, a cable 7 may be removablely arranged in the recess 6. For example, the recess 6 may stationarily hold or grip the cable 7, such as through friction or a crimping or gripping force of the recess 6.

The active side portion 4 of the earphone is configured to be inserted in connection to an auditory canal in a user's ear 20 in order to enable the user to listen to audio output transmitted via the earphones. For example, the active side portion 4 may be slightly tapered for enabling a close fit to the user's auditory canal. The active side portion 4 may be formed by a soft and partially resilient material so that the earpiece 2 provides a comfortable fit in a user's ear, and to prevent rubbing. The active side portion 4 and the front side portion 3 may be different materials, or they may be the same materials. In an example, the front side portion 3 may be of a polymer material, steel, or other material, as only examples. For example, it may be an advantage if the material of the front side portion 3 is a hard or firm material, and/or a wear resistant material, e.g., so as to protect the components inside the earpiece 2.

The front side portion 3 and/or the active side portion 4 may be configured so the earphone may be entirely or mostly retained inside the outer ear, such as to not extend outside of the ear, which may make the earphone suitable for use in a wide range of activities or states of the user. For example, in the example where the earphone is configured to be entirely or mostly retained inside the outer ear, the earpiece 2 may not disturb sleeping even if the user is resting on the side of their head, such as with the ear being supported by a pillow or the like, since the earpiece 2 does not, or does not mostly, extend outside of the outer ear.

FIG. 2 illustrates a front view of an earphone according to one or more embodiments. As illustrated in FIG. 2, the cable 7 may be attached to the earpiece 2 at a first end 10. For example, when the cable 7 is configured to include a communication interface or wired cabling connecting the earpiece 2 to a remote control unit and/or microphone, or a remote control unit, microphone, and/or media player when the cable 7 is alternatively or additionally wiredly connected to a media player compared to a wireless embodiment, the first end 10 may include or represent an orifice or opening in the rim 5, the active side portion 4, and/or the front side portion 3 to provide further communication between the internal communication interface or wired cabling of the cable 7 to internal components of the earpiece 2. Alternatively, the first end 10 may be representative of a connection unit or interface where the cable 7 terminates and through which electrically connects to the internal components of the earpiece 2. The recess 6 may be configured or arranged at or along a second end 11 of the earpiece 2, such as illustrated in FIG. 2 in physical arrangement with the front side portion 3 and rim 5. As noted above, the recess 6 at or along the second end 11 may be configured or arranged on or in the front side portion 3, the active side portion 4, and/or the rim 5. In an example, such as illustrated in the example of FIG. 2, the second end 11 may be a portion of the earpiece 2 physically arranged on an opposite portion of the earpiece 2 at the first end 10. For example, by placing an entrance position of the cable 7 at the first end 10 at the first side portion 3 and rim 5 of the earpiece 2, and the recess 6 on the example opposite side of the earpiece 2 at the second end 11, the loop may be adjustable or expandable to have a shape as similar to the curve of the concha of the ear of the user as possible.

The recess 6 may be arranged either on an outer portion of the earpiece 2, such as the example second end 11, or more centrally, such as more centrally on the front side portion 3, as only an example. The recess 6 may extend in a direction in line with, at an angle to, or perpendicularly relative to the entrance of the earpiece 2 at the example first end 10. Also, in an example, the front side portion 3 may have a convex exterior surface, e.g., the surface of the front side portion that is away from the ear, and may be configured to, when in use, be substantially level or even within a plane represented by the user's outer ear surface, such as the auricle, rim, helix, or pinna of the ear. Thereby, any sharp scrubbing edges of the earpiece 2 may be avoided which may be uncomfortable for the user. Further such a configuration may allow a user to rest the ear 20 against an object, such as a pillow, without the earpiece 2 obstructing the comfort for the user.

FIG. 2 also illustrates an example where the cable 7 is arranged in the recess 6 along the length of the cable 7. This example may provide a slidable arrangement of the cable 7 in the recess 6. For example, by arranging the cable 7 in the recess 6, an adjustable loop 9 may be formed in the cable 7 between the first end 10 and the second end 11. In an example, the recess 6 may stationarily hold, grip, or fix the cable 7 so the loop 9 may be fixedly or stiffly maintained, such as so the loop 9 may be fixedly placed in or relative to the concha of a user's ear to maintain a position of the earpiece 2 relative to the ear. For example, the recess 6 may be configured so the cable 7 is slidably arranged in the recess 6, such as to provide the adjustable or expandable loop 9 arranged to run along the curve of the concha in the ear 20 in order to provide stability for the earphone 1 to help prevent the earpiece 2 from accidently falling out of the ear 20. Here, though cable 7 is described as connecting internal cabling of the cable 7 to internal components of the earpiece 2 through the opening of the earpiece 2 at the first end 10, the cable 7 is not required to connect to internal components of the earpiece 2, and thus, the opening of the earpiece 2 at the first end 10 may not be required. Rather, the first end 10 may alternatively hold or grip the cable 7, such as through another recess similar to the recess 6, to provide the slideable or expandable loop 9 for maintaining the position of the earpiece 2 relative to the ear and in cooperation with recess 6.

Figure 3:
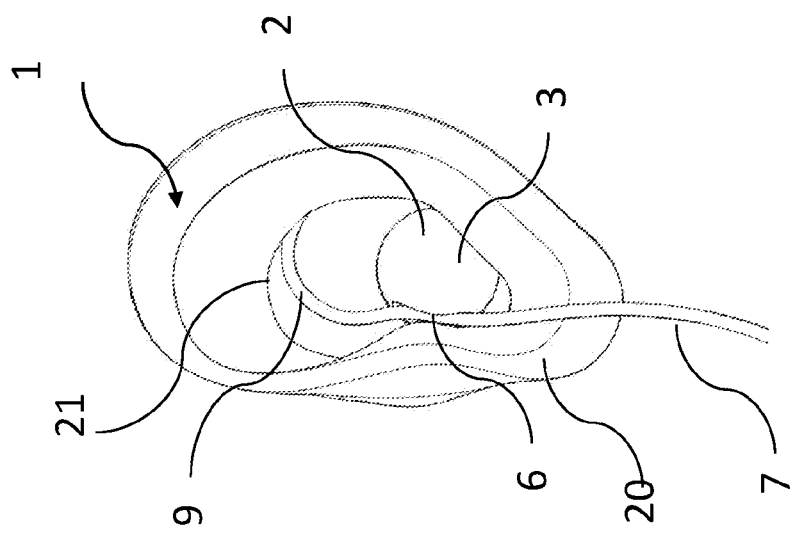
FIGS. 3-4 illustrate a front view of an earphone in use according to one or more embodiments.
Figure 4:
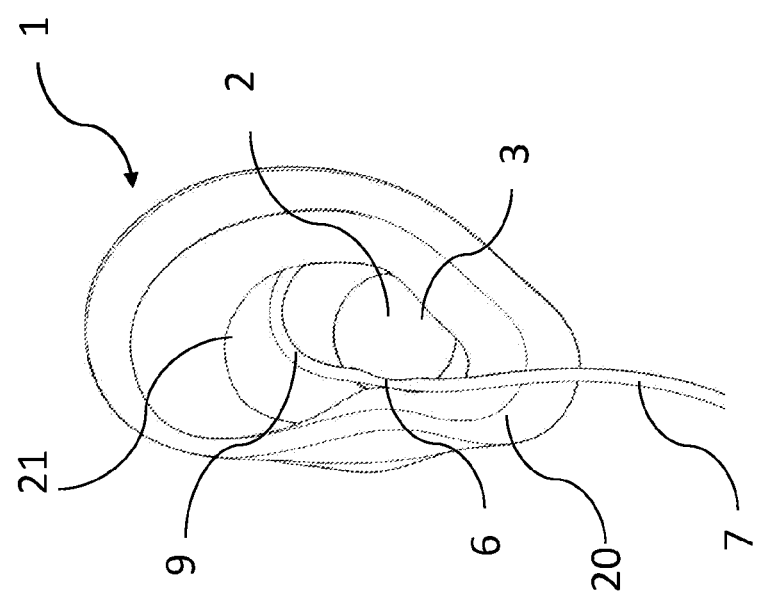

For example, FIGS. 3-4 illustrate a front view of an earphone in use according to one or more embodiments, where the loop 9 is illustrated as being placed in the concha 21 of the user's ear.

Here, depending on embodiment and the variability of configured holding force of the recess 6, the loop 9 may be adjustable in order to allow a pressing action against the ear 20 when pressing against the concha 21 in order to retain the earpiece 2 inside the ear 20 of the user. FIGS. 3 and 4 illustrate separate examples of how the size of the loop 9 may be variously adjusted to have a tailored fit for the user's ear 20, such as by variously sliding the cable 7 in the recess 6. Thereby the loop size may be adapted to the user's ear and thereby have a tailored fit. For example, FIG. 3 demonstrates that the loop 9 with an adjusted shorter or smaller size may fit ear 20 differently from a longer or greater size may fit ear 20 in FIG. 4, so the user may be able to variously adjust the loop size to have a tailored fit to maintain the earpiece 2 within the user's ear 20. For example, the loop 9 may thereby hold or fix the earpiece 2 inside the ear 20 and prevent the earpiece 2 from falling out during, for example, sleeping, running, dancing etc. etc.

As an alternative, the cable 7 may be configured to merely connect to internal components of the earpiece 2 through either of the example first end 10 or second end 11, or other portion of the earpiece 2, and the loop 9 may be a separate cable or stiff element or frame configured between the non-limiting example first end 10 and second end 11.

Figure 5:
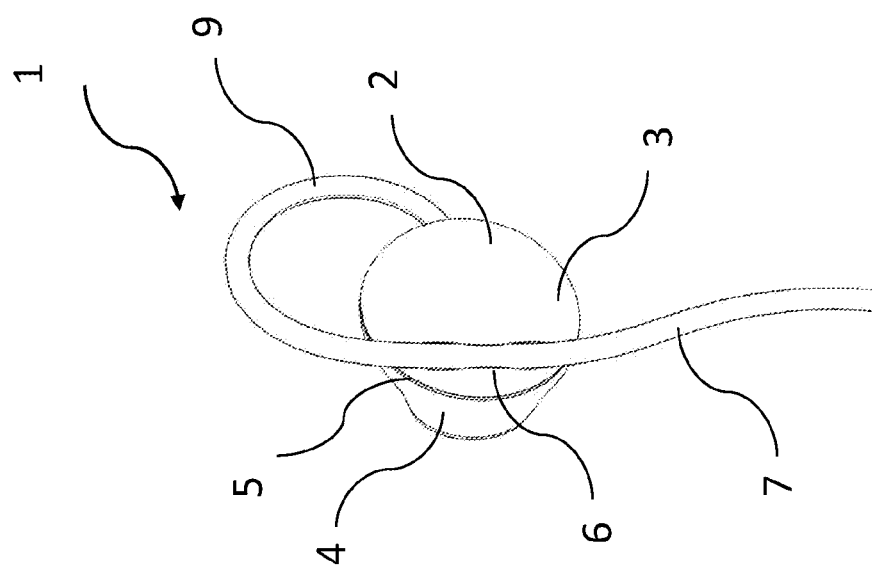
FIG. 5 illustrates a perspective view of an earphone according to one or more embodiments.

FIG. 5 illustrates a perspective view of an earphone according to one or more embodiments. Referring to FIG. 5, the active side portion 4 is shown protruding from the earpiece 2, such as in the aforementioned example configurations for insertion into the user's ear canal.

Here, though examples have been discussed regarding the configuration of the active side portion 4 being an in-ear active side portion 4, embodiments are not limited thereto. For example, the active side portion 4 may be an out of ear active side portion 4, to sit or rest outside of the user's ear canal. For example, when the active side portion 4 is configured to sit or rest outside of the user's ear canal, a side pressure from a pillow, for example, acting on the earphone while resting the head against the pillow may not apply pressure on the sensitive ear canal, thus providing an earphone further adapted for sleeping. Also, as noted above, in an example the earpiece 2 is configured to be retained inside the outer ear and not extend outside of the ear, which may make the earpiece 2 further suitable for use in a wide range of activities or states of the user. For example, if the earpiece 2 is retained inside the outer ear and/or the active side portion 4 is an out of ear active side portion, the earpiece 2 may not disturb sleeping even if the user is resting the ear on a support like a pillow or the like. As an alternative, the active side portion 4 may be interchangeable between the in-ear and out of ear configurations, and/or for respectively different sizes for fitting for various user's ears.

Figure 6:
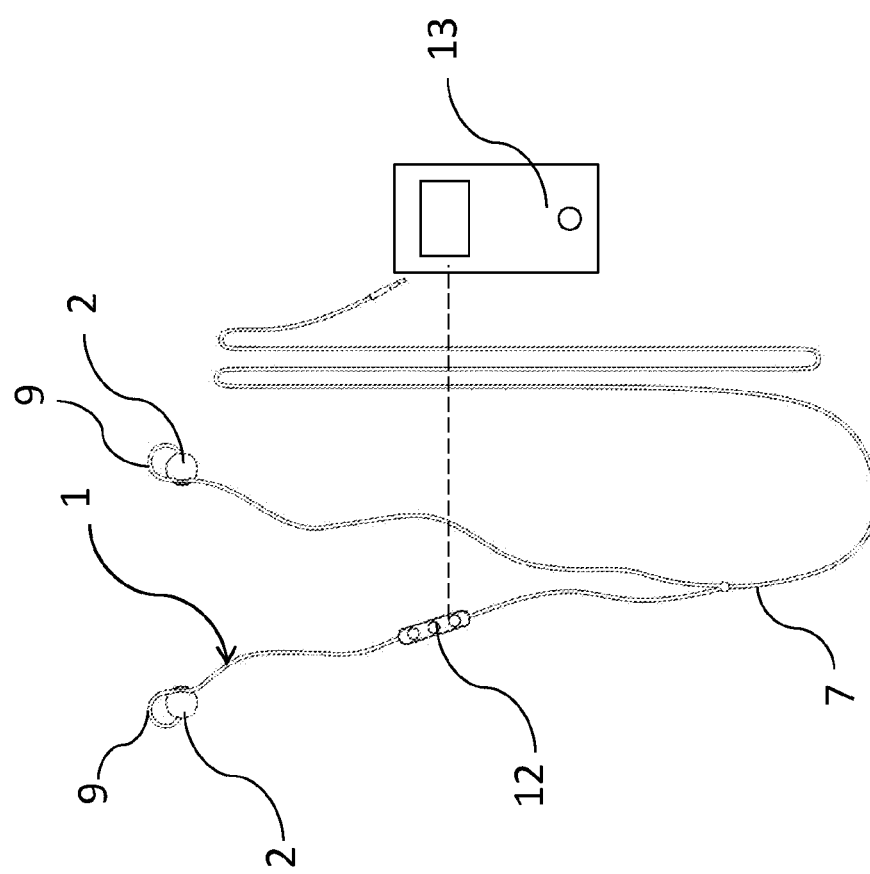
FIG. 6 illustrates an earphone system according to one or more embodiments.

FIG. 6 illustrates an earphone system according to one or more embodiments. Referring to FIG. 6, the earphone system includes earpieces 2, with respective loops 9, cable 7, a remote control unit 12, and media player 13. The remote control unit 12 may be arranged along or in-line with the cable 7 of the earphones. In this example, the remote control unit 12 is connected via a cable 7 to control operations of the media player 13, such as for selective control for the audio output of the media player 13 or for performing other non-audio output related operations of the media player 13. The media player 13 may also be any computing device that is configured to provide or stream audio either wirelessly and/or through one or more wires, such as cable 7. For example, the media player 13 may be a mobile phone, wearable smart device, tablet, exercise equipment, television, stereo receiver, etc. Thus, the remote control unit 12 may connect with either or both of the earpieces 2 through cable 7 and/or wirelessly, such as in an alternate example where the media player 13 communicates with the earpiece 2 and the remote control unit 12 through a wireless communication protocol, such as Bluetooth, WiFi 802.11 compliant network, or other communication protocol, including ad hoc networks.

In addition, in an example, the remote control unit 12 is wirelessly connected to either or both of the earpieces 2 and the media player 13, while the earpiece 2 is connected through cable 7 to the media player 13. For example, the remote control unit 12 may be selectively attached the cable 7 or operable separate from the cable 7 when connected to, or including, a corresponding power source.

Figure 7:
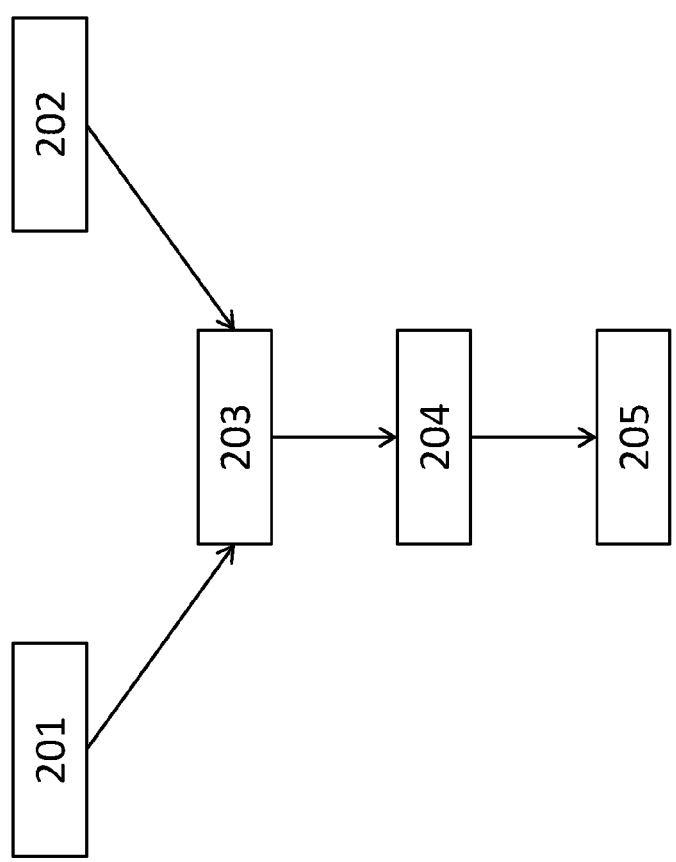
FIG. 7 illustrates a flow chart describing an earphone method according to one or more embodiments.

FIG. 7 illustrates a flow chart describing an earphone method according to one or more embodiments, such as implemented by the above earphone system of FIG. 6 and/or below discussed earphone system of FIG. 8, as only examples. Thus, though the operations of FIG. 7 will be explained through reference to similar reference numbered components as in FIG. 6 or FIG. 8, and thereby imparts the availability of such example operations on the earphone systems of FIGS. 6 and 8, or any of the remaining previous discussions, this is for explanatory purposes, and thus embodiments are not limited thereto.

Referring to FIG. 7, one or more earphones may be configured in an earphone system that includes a remote control unit 12 attached on a cable 7 used to connect one or more earphones to the media player 13. In addition, while some earphones may communicate wirelessly with either or both of corresponding remote control units 12 and the media player 13, other earphones in the earphone system may communicate through corresponding cables 7 with either or both of corresponding remote control units 12 and the media player 13. Alternatively, in an example, the remote control unit 12 and/or either or both of the earpieces 2 of an example earphone may communicate via a wireless protocol with the media player 13. The wired and wireless communications in these settings may include wiredly and/or wirelessly preparing/transmitting/receiving any or any combination of control data to/from one or more of the earpieces 2 of corresponding earphones, to/from corresponding remote control units 12, and/or to/from the media player 13 to control the respective audio output of any of the one or more earpieces of one or more earphones in the earphone system dependent on respectively determined states of the corresponding listeners. For example, one or more of the earphones may communicate the control data wirelessly with the media player 13 and one or more corresponding remote control units 12, and the one or more corresponding remote control units 12 may communicate control data through one or more example cables 7 with the media player 13, or one or more of the earphones may communicate control data through the one or more example cables 7 with the media player 13 and one or more corresponding remote control units 12, and the one or more corresponding remote control units 12 may communicate the control data wirelessly with the media player 13. As another example, the one or more earphones may communicate control data wirelessly with the media player 13, and the one or more earphones may communicate through one or more cables 7 with the one or more corresponding remote control units 12, which may communicate through one or more cables 7 with the media player 13, or the one or more earphones may communicate control data through one or more corresponding cables 7 with the media player 13, and the one or more earphones may communicate wirelessly with the one or more corresponding remote control units 12, which may communicate wirelessly with the media player 13. Still further examples are available, such as an all wired environment, an all wireless environment, there being multiple media players in the earphone system.

In these examples, the wired or wireless communication control data may also include sensor data, e.g., collected by one or more of earpieces 2 of the one or more earphones or the corresponding remote control units 12, to be analyzed by the one or more earpieces 2, the corresponding remote control units 12, the media player 13, and/or one or more remote servers remotely connected to the media player 13, to determine a state of a respective user, the determination of which can subsequently be relied upon by any of the one or more earpieces 2 of the one or more earphones, corresponding remote control units 12, or media player 13 to control the output of the audio output for that respective user.

As only an example, the control data may also be control data to control a selecting or implementing of specific tracks, playlists, genres, BPM-tracks, adjusting volume, pausing, stopping, playing, etc., such as based on the determined state of the user and/or indicating predetermined, or user preset, corresponding controls that will be implemented for various determinable states of the user. Based on such examples, FIG. 7 illustrates operations for adjusting an audio output from the media player 13 by one or more earpieces 2.

Figure 8:
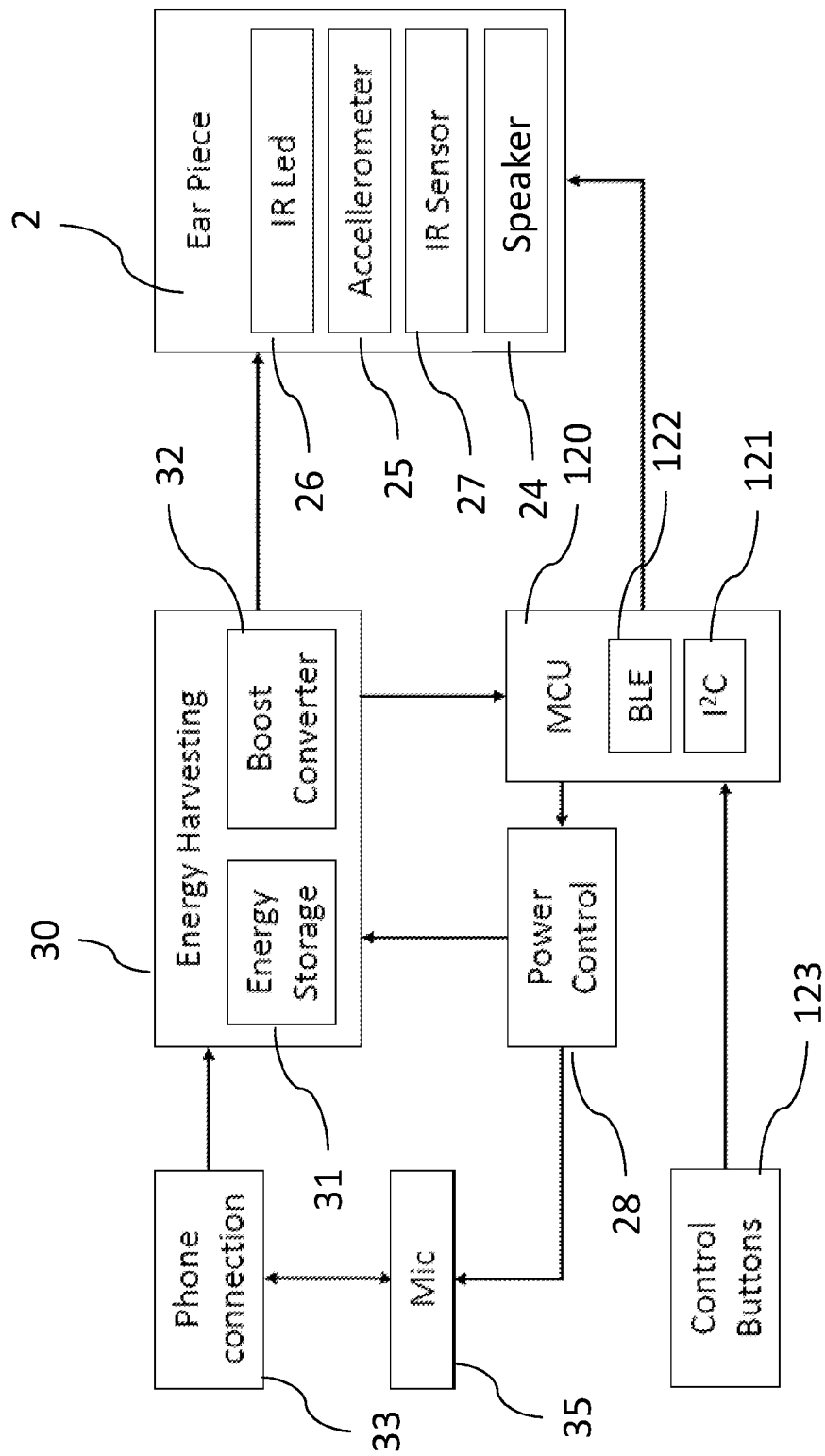
FIG. 8 illustrates an earphone system according to one or more embodiments.

In this example, and with further reference to the example earphone system of FIG. 8, one or more of the earpieces 2 may each include a speaker element 24 for converting an audio output into sound waves, a controller 120, a first motion sensor 25, and pulse rate detector, e.g., including an example IR led 26 and IR sensor 27, noting that additional or alternative motion and bio-sensor detectors may be available.

In FIG. 7, a detecting operation 201 is performed by the controller 120 to control the motion sensor 25, and thereby detect movements of a user based on movement detections by the first motion sensor 25, which is configured to generate sensor data representative of or indicating movement or changes in movement. A pulse rate detecting operation 202 is also performed by the controller 120, where the controller 120 controls the detecting of a pulse rate through control of the pulse rate detector, which is configured to generate pulse rate sensor data indicating a measured pulse rate of the user or other bio-signal data. As illustrated in FIG. 7, operations 201 and 202 may be performed in parallel, noting that embodiments are not limited thereto.

In operation 203, the respective sensor data generated in operations 201 and 202 may be transmitted to the controller 120. For example, the controller 120 may control the motion sensor 25 and the pulse rate detector to transmit their respectively measured sensor data to the controller 120.

In operation 204, a state of the user is determined by the controller 120, for example. The state of the user may be determined by the controller 120 based on the received sensor data from the motion sensor 25 and the received sensor data from the pulse rate detector.

In operation 205, based on a result of operation 204 with respect to the determined state of the user, the controller 120 may control selection or adjustment of audio playback or audio output of the media player 13, for example. In an example, the controller 120 may control the media player 13 to select or adjust audio output for provision to the earpieces 2, such as through the aforementioned wired or wireless transmission of control data from the controller 120 to the media player 13, and thereby control the media player to provide the selected or adjusted audio output to the speaker elements of the earpieces 2. If the controller 120 is performing operations of the media player 13, then the controller selects or adjusts audio output and provision of the selected or adjusted audio output to the speaker elements of the earpieces 2.

Accordingly, operation of the media player 13 and the earpieces 2, for example, may be controlled by the controller 120 based on consideration of both measured movement data and measured bio-sensor data of the user as collected by of one or more of the earpieces 2.

FIG. 8 illustrates an earphone system according to one or more embodiments. The earphone system of FIG. 8 may correspond to the earphone system of FIG. 6, and implement the operations of FIG. 7, though embodiments are not limited thereto. Thus, while components of FIG. 8 may be explained through reference to similar reference numbered components as in any of the above discussions, and thereby imparts the availability of such example operations or components on the earphone system of FIG. 8, this is for explanatory purposes, and thus embodiments are not limited thereto.

With respect to FIG. 8, the earphone system includes an example earpiece 2, energy harvesting component 30, and controller 120, for example, which may be implemented in a wired, wireless, or combination of wired and wireless environments. The earpiece 2 includes a speaker element 24 for playback of audio output, a motion sensor 25, and a pulse rate detector. In an example, the motion sensor 25 is an accelerometer. The pulse rate detector may include an IR led 26 and an IR sensor 27, as only an example. The pulse rate detector may alternatively be another bio-signal detector.

In an example, the motion sensor 25 is an accelerometer adapted to sense motions of the user. For example, the accelerometer may be a 3D accelerometer. By allowing the motion sensor to be an accelerometer, it may be possible to instantly detect a change in the motion pattern of a user, as well as monitor trends in motion. A user may for instance at a certain time be walking, and at a time later start jogging. The accelerometer detects accelerations, i.e. changes in movements. The acceleration or movement pattern would be different between when the user walks, jogs, or sprints, for example. As the accelerometer detects such changes in motion, the example controller 120 may receive the corresponding sensor data from the motion sensor 25, determine the state of the user, and control the earphones according to a predetermined setting. In an example, one or more motion sensors may be located in one or both of the earpieces 2 of an example earphone. These motion sensors may be referred to as first motion sensors, for example. Thereby, through measurements of these one or more first motion sensors, motions of the users head may be registered.

Further, the IR sensor 27 may sense the reflected light from the IR led 26, and from that reflection, the pulse rate detector may detect and calculate the blood flow and consequently the pulse rate. Alternatively, the sensed data of the reflected light by the IR sensor 27 may be transmitted to the controller 120, for example, where the controller 120 calculates the blood flow and consequentially the pulse rate. In an example, the IR led 26 uses a wavelength of about 800-900 nm, e.g. about 850 nm. In an example, each earpiece 2 may include pulse rate detectors, or one or both of the earpieces 2 may include multiple pulse rate detectors, which may provide improved accuracy in determining the state of the user.

By using the IR sensor 27, it may be possible to detect the blood flow without having an external pulse rate detector device in close connection to the body, such as strapped or taped. The IR sensor 27 may be placed in or on one or more of the earpieces 2 at a place to be closely positioned to a user's body. For example, the IR sensor may be placed in or on the active side portion 4 of the earpiece 2 that is being inserted into the ear or being held close to the ear. By placing the IR sensor in or on the earpiece 2, the blood flow may be detected from a spot in the ear. IR sensors may further be easy to use and may not require any further installation on the body. Here, though such an IR sensor pulse rate detector has been discussed as an available example, embodiments are not limited thereto. For example, a conductive sensor material for detecting the electrical conductivity of the user's skin may additionally or alternatively be used to determine the pulse rate of the user.

In an example, in addition to using sensor data from the motion sensor 25, i.e., referred hereinafter as the first motion sensor 25, for determining the state of the user, because the first motion sensor 25 may detect minor relative motions between the earpiece 2 and the ear, the sensor data from the IR sensor 27 may be filtered so as to avoid disturbance sensor data by filtering out motion artifacts that correspond to the detected relative motions between the earpiece 2 and the ear of the user as detected by the first motion sensor 25.

In addition, a second motion sensor, e.g., a second accelerometer, may be implemented in a remote control unit 12, such as the remote control unit 12 of FIG. 6, and may be provided for further improved accuracy in determining the state of the user, e.g., in addition to the use of the first motion sensor 25. A second motion sensor may additionally or alternatively be implemented in the media player 13, with any or any combination of the first and second motion sensor data being used to determine the state of the user. In an example, only one earpiece 2 may include the first motion sensor 25 and the example pulse rate detector, or only one of the earpieces 2 includes the first motion sensor 25 and the other earpiece 2 includes the pulse rate detector, or when both earpieces 2 include both motion and heart rate sensors only one sensor/detector may be selectively operated in each earpiece 2. In an example, with respect to the motion sensor 25 in the earpiece 2, by only having sensors in one earphone the costs may also be kept lower. Moreover, in an example, sensor data transmitted from the IR-sensor may be analog data or in an analog signal form, though embodiments include either detector or sensor data to be transmitted to the controller 120 as analog signals and/or digital signals.

Here, in the example where the earphone system further includes the example remote control unit 12 of FIG. 6, the controller 120 may be included one or both of the earpieces 2 that are separate and at a distance from the remote control unit 12. The remote control unit 12 may communicate with the earpieces 2 through the example cable 7 of FIG. 6 or wirelessly. Alternatively, the remote control unit 12 may include the controller 120 and the second motion sensor. Though examples are provided where the second motion sensor is included in the remote control unit 12 or the media player 13, embodiments are not limited thereto. In FIG. 8, the remote control unit 12 may be represented by control buttons 123, for example.

The user may use the remote control unit 12 to manually control the audio output, or alternatively the user may use the earpieces 2 to manually control the audio output. Moreover, the second motion sensor may be used in combination with the first motion sensor 25 to determine motions of the user with even higher accuracy. Further, by having two motion sensors, sensor data from both first and second motion sensors may be used in the determining of the state of the user, or the sensor data from the first motion sensor 25 may be used for filtering the detected pulse rate, e.g., so as to avoid disturbance or artifact sensor data resulting from relative motions between the earpiece 2 and the ear of the user, and the sensor data of the second motion sensor may be used in combination with the filtered heart rate data to determine the state of the user. In an example, the second motion sensor may be a second accelerometer.

Moreover, the illustrated controller 120 may be a micro controller 120 that is communicatively connected to one or more of the earpieces 2. In examples, the controller 120 may be an included component of one or more of the earpieces 2. A control of the adjustment or selection of audio output by the controller 120 may be automatically or autonomously performed by the controller 120. In another example, one or more of the sensor data from the first motion sensor 25 and pulse rate detector may be offloaded to the media player 13, for example, and one or more of the operations to determine the state of the user and the providing, adjusting, and/or selective playing of audio output through the speakers of the earpieces 2 may be performed in a distributed manner. Thereby, in an example where the controller is at least one of the earpieces 2 or the remote control unit 12, some of the calculations that are performed to determine the state of the user and/or the providing, adjusting, and/or selective playing of audio output may be distributed between the controller 120 integrated in the earphones and the media player 13 having a higher calculation capacity, or all such calculations may be performed by the media player 13.

In an example, communication between the earpieces 2 may be implemented through the cable 7, such as illustrated in FIG. 6. The cable 7 may include a signal cable dedicated for digital communication, as well as audio signal cables. For example, a dedicated cable for the sensor data may be used. Alternatively, as noted above, any of the communication may be implemented wirelessly.

As noted above, the controller 120 may be, or arranged in, the aforementioned example remote control unit 12 of FIG. 6, for example, and/or configured in either or both of the earpieces 2. The controller 120 may be a microcontroller, for example. The controller 120 and the remote control unit 12, such as when the remote control unit 12 and the controller 120 are separate components of the earphone system, may each include an I$^2$C circuit 121 configured to respectively provide communication with other components of the earphone system, such as between the controller 120 and the example remote control buttons 123 and/or from the pulse rate detector, e.g., either or both of sensors 26 and 27, and the first motion sensor 25. Moreover, the controller 120 and the remote control unit 12 may each include a wireless communication module, which is hardware communication circuitry, such as a Bluetooth circuit for wireless communication, e.g. a Bluetooth low energy (BLE) 122 or 802.11 Wifi circuit or other standardized wireless communication protocol, such as a protocol that has such lower power consumption capabilities, configured to provide wireless communication to/from the media player 13, or other devices, as discussed above. The communication module, or another hardware communication module may be configured to also implement cellular or other telecommunication protocols, such as 3G, 4G, 4G LTE, 5G, etc. In an example, the controller 120 may be included in one or more of the earpieces 2 and the remote control unit 12 may be arranged on the example cable 7 connecting the earpieces 2 and the media player 13 when the earpieces 2 connect wiredly to the example media player 13, for example. When the earpieces 2 connect wirelessly with the media player 13, the remote control unit 12 may connect wirelessly with either or both of the earpieces 2 and the media player 13 or wiredly with the earpieces 2 and wirelessly with the media player 13. Alternatively, the remote control unit 12 may be configured to perform the operations of the media player 13. Still further, in an example, the illustrated controller 120, energy harvesting component 30, power control 28, microphone 35, and phone connection 33 may be configured in one or both of the earpieces 2, or distributed between the earpieces 2 of an example earphone system. In such an example, the remote control unit 12 may be physically separate from the earpieces 2, and either of the earpieces 2 or the remote control unit 12 may perform the operations of the media player 13. Still further, in such an example, the phone connection 33 of the earpieces 2 and/or a like component of the remote control unit 12 may include phone communication hardware, such as for making and receiving phone calls or data. Still further, in another example, the phone connection 33 of FIG. 8 is representative of a mobile processing device, such as a smart phone or tablet having a user interface, such as for controlling selecting of user determinable states and corresponding associated audio controls or adjustments discussed herein, and one or both of the earpieces 2, e.g., the controller 120 in at least one of the earpieces 2, and the remote control unit 12 may be configured to communicate with the phone connection 33.

Accordingly, the controller 120 may determine, based on respective motion and heart rate sensor data, that the user is falling asleep, and accordingly then control a volume of audio output to be lowered, a specific song or genre to be selected, or a playlist pre-associated with sleeping be activated, e.g., in order to not risk that the user may wake up abruptly due to high noise. In another example, if the controller 120 determines based on the respective motion and heart rate sensor data that the user is starting or beginning to work out, the volume may be increased, a different genre selected, or a playlist pre-associated with working out may be activated. More specifically, the sensor data from the respective sensors may be analyzed, a result of which differentiates between different activities of the user, e.g., between running and lifting weights at the gym, and the controller 120 can then adjust the audio output accordingly.

Here, the user may preset such playlists that are to be associated with multiple different determinable states, such as through a user interface of the media player 13 or another device user interface, such as a smart phone, that is in communication with the controller 120. Thereby, the user may select music or other audio which is suitable for the detected state of the user, in addition to the availability to adjust volume, pause or stop the audio etc., in response to the determination of the state or state change. In addition, how audio output is adjusted for differing states or changes in states may be implemented by the controller 120 according to a user pre-defined setting associated with the determined state of the user. Thus, the user may self choose how the audio output is to be changed depending on differing determinable states of the user, as well as the example self choosing of types of music, genre, or playlists. The settings may be handled through the example user interface of the media player 13 or of the other device, such as a connected smart phone. The control of the audio output may be predefined by the user for any specific state that a user may find appropriate. For instance, a user may upload to the media player 13, or identify the location or name of the same, a playlist of music, a genre, or an audio book that may be suitable when in a resting state, or choose to pause the audio or decrease the volume if the controller 120 determines that the state of the user is the falling asleep state. Another playlist of audio may be defined to be played when a work out state is determined by the controller 120. Alternatively, or as a complement, the user may predefine a variety of sound content which beats per minute correspond to different user states, and the controller may control the audio output accordingly. In an example, the user may also at any time manually override the determined state-based control of the media player 13, e.g., if a certain audio output may not be desirable at a given time, such as through controls of the example remote control unit 12 or the touch or tap controls of the earpiece 2, for example.

In addition, in an example where the audio output is music and controlled based on predetermined association with the detected state of the user, the controller 120 may further perform a matching of the music's beat per minute (bpm) with the detected activity by the first motion sensor 25. For example, the controller 120 may control the audio output to be a selected music that has a related beat to the state of the user, such as a song with fast pace (high BPM) being controlled to be played when the user is determined to be running at a high speed (e.g., based on a detected high heart rate) during a determined running state (e.g., based on the detected high enough heart rate and detected sufficient motion), while a song with a slower pace (slower BPM) may be controlled to be played when the state is determined to be a slower running or jogging (e.g., based on a detected lower heart rate) during the determined running state. The controller may thereby choose music according to its properties, such as beats per minute, frequency and such in order to match a user's state with the right music that may be suitable for the corresponding activity or state. Thus, in examples, audio output may be based on the determined state of the user dependent on both the detected pulse rate and the detected motion, and further the music's beat per minute (bpm) may be adjusted to correspond to the detected pulse rate. By adapting the controller 120 to be able to perform such a matching between a user's detected pulse and a piece of music's beat per minute, it may facilitate for the user to be provided a piece of music most suitable or most desirable to the user's state. Moreover, the matching of the music's beat per minute (bpm) may be based on a detected cadence of the user. The cadence may be, for example, the number of revolutions of a crankset of a bicycle per minute when the determined state is bicycling, or a step frequency of the user when the determined state is walking or running. For instance, if the user is bicycling, the controller 120 may obtain cadence sensor data from a sensor integrated in or attached to the bicycle, or other machine, to determine the cadence for the matching. In addition, if the user is running, and periodically starts sprinting, the change in pulse/cadence may also be detected and the controller 120 may receive the changed motion data and adjust the audio output to a music that has substantially similar or at least related beats per minute as the user's new or alternating pulse/cadence. Thereby the user does not have to manually adjust the music, which is desirable to avoid during a workout since any manual adjustment may be time-consuming and taking focus from the physical activity.

In another example, if a user is awake and walking, the respective sensor data from the heart rate detector and the first motion sensor 25 may in combination provide sufficient data to the controller 120 for the controller 120 to discern a correct state of the user and control a provision of correct audio output and/or adjustment of already provided audio. If such a user subsequently sits down, the pulse rate detector may generate sensor data that indicates a slower pulse and the first motion sensor 25 may generate sensor data that indicates a motion pattern associated with sitting, which may be sufficient data for the controller 120 to determine that the state of the user is resting, and to control a change in audio output, such as by controlling a decreasing in the volume of the audio output or a switch in the audio output to a low beat (beats per minute) music audio output. Still further, if the controller 120 determines that the state of the user thereafter changes to the user beginning to fall asleep, or having fallen asleep, while listening to audio output, the control 120 may further lower the volume of the audio output or alter the audio output, and/or may then further cease the audio output based on the detected changed state of the user.

Thus, in an example, the determination of the state of the user includes determining whether the user is asleep or awake, which may still further include determining whether the user is falling asleep from an awake state and whether the user is waking from a sleep state. For example, by combining data of a measured pulse rate and sensed motion of the user, asleep, if the pulse is determined to have slowed down to a rest pulse and the controller 120 further determines that there has not been sufficient change in motion over time, the controller 120 may determine that the user is in a sleep state. For example, the controller 120 may determine that the detected pulse rate is a resting pulse rate and that a detected motion sensor sensing corresponds a moving pattern pre-associated with sleeping, and be able to determine that the user is in the asleep state. Here, the example moving pattern that is associated with sleeping may be adjusted over time as the user uses the earphones. In other examples, the moving pattern that is associated with sleeping may correspond to aggregated detected movements over time being below a threshold value. In another example, the controller 120 may control the audio output to be gradually adjusted when the determined state is that the user is falling asleep, such as by gradually decreasing the volume during a determined time span where the user is gradually falling asleep. In an example a resting pulse rate may also be predefined by the user and/or the resting pulse rate may be automatically determined and adjusted over time by the controller 120 and or machine learning implemented by the controller 120 or the media player 13.

In another example, the controller 120 may further determine whether the state of the user is the resting state or whether the user is in a working out state.

Thus, the controller 120 may control the audio output to be adapted to the determined activity state of the user. For instance, the controller 120 may determine that there is a combination of a detected low pulse rate and a detected slow or minimal motion, so the controller 120 may determine that the user is in the rest state. Here, for example, the rest state may be distinguished from an asleep state in that the detected pulse rates and/or the detected moving patterns are different between the rest state and the asleep state. Moreover, a user being at rest may be more probable to desire a different audio output than when the same user is working out. For example, the controller 120 may determine that the state of the user is a working out state, e.g., including the controller 120 determining between plural working out sub-states of running, lifting weights, bicycling, climbing, dancing, jumping, doing yoga, stretching, etc. Each of the sub-states of the workout state may be determined based on different detected heart rate ranges, for example, within detected heart rates that are interpretable to be the workout state. The controller determinable working out state(s) may also be defined by the user in a user interface of another device, e.g., a smart phone, that is connected to the controller 120 or a user interface of the media player 13. Location information may also be generated or obtained by the earphones, the controller 120, or the media player 13, such that when the user is determined to be visiting a gym, the controller 120 may automatically control the audio output to provide "bicycle race" by Queen at high volume when the determined sub-state is a warming up a spinning bicycle, to provide "Eye of the tiger" by Survivor while when the determined sub-state is a bench pressing state, to provide "I will survive" by Gloria Gaynor when the determined sub-state is a burpees exercise state, and/or to provide "No woman no Cry" with Bob Marley at a low volume to the user when the determined sub-state is a stretching state. Thus, based on this progression, for example, the controller 120 may also consider preset or learned progressions of such different exercises, or activity sub-states, to determine the activity state of the user, such as for the example gym location. In these examples, the different audio or volumes may be based on predetermined, e.g., by the user or by a manufacturer, preferences of the user, such as the user being more likely to prefer higher volume when running compared to when stretching after the run.

In an example, sensor data from either or both of the first motion sensor 25 and the second motion sensor may indicate any change in a user's movements and the sensor data from the pulse rate detector may be used to determine in what state on a sleep-to-workout-scale the user is in. By combining the sensor data from the first motion sensor 25, for example, and the sensory data from the pulse rate detector, information about a user's state may be determined with higher accuracy than previous attempts that based the user's activity only on a single type of sensor data, for example.

Herein, a "state of the user" is to be broadly understood as referring to a user's physical state or activity. It includes, but is not limited to, user states like the user being awake, resting, sleeping, working out, running, lifting weights, bicycling, climbing, dancing, jumping, etc. Further, the state of the user also includes transition states of going from awake to falling asleep, such as gradually falling asleep, and consequently based on such a determined transition state the controller 120 may lower the volume of the audio output gradually. Moreover, the different detectable or discernable states of the user may also be predefined by the user, including adding to or deleting from any preset states that may have been predetermined by a manufacturer, such as through a user interface of the media player 13 or through a user interface of an application on another device, such as a smart phone, that is in communication with the controller 120. Thereby, if the user wants the earphones to be able to detect a specific state, say dancing, the user can define the state dancing and corresponding respective dancing state indicating motion and heart rate sensor data. Moreover, the controller 120 may further include computer readable code or have a machine learning configuration that learns the user's different states and corresponding respective sensor data. Thereby, the controller 120 can further improve its ability and accuracy to determine the state of the user.

Moreover, a power control unit 28 may be included in the earphone system for controlling when the different components are to be activated, deactivated, and inactive. The power control unit 28 may also be electrically coupled to the energy harvesting component 30 including an energy storage circuit 31 and a boost converter circuit 32, for example. The energy storage circuit 31 may include a micro capacitor, though embodiments are not limited thereto. As only an example, the energy harvesting component 30 may include trickle charge circuitry configured to harvest energy from the phone connection 33, such as an example where the energy harvesting component 30 harvests energy from a 3.5 mm plug at a terminating end of the cable 7 where energy may be harvested from the played audio provided through cable 7 or a microphone line included in the cable 7. Here, this discussion of the energy harvesting component 30 is an example of implementation of the energy harvesting component 30 in a wired environment, while embodiments are not limited thereto as additional and/or alternative embodiments are also available. For example, the energy harvesting component 30 may harvest energy from any other type of phone connections or transmissions of the phone connection 33, non-phone connections or transmission, or any other type of radiated or transmitted energy. With the energy harvesting component 30 no internal or external battery may be needed, or smaller sized batteries may alternatively be available, e.g., compared to a system without such an energy harvesting capability, and the energy harvested by the energy harvesting component may be used to boost the internal battery reserves of the controller 120, such as where the controller 120 is included in one or more of the earpieces 2, which enables a more compact design. For example, with the energy harvesting component 30, no exterior charging or replacing of batteries may be needed for the measuring of motion or pulse rates. For example, by having a local energy storage circuit 31 and a boost converter circuit 32 the motion sensors(s) and the pulse rate detector(s) may be selectively operated or driven with enough energy during active periods, e.g., without an external power source. For example, the energy harvesting component 30 may be controlled to harvest energy during inactive periods, such as when the user is determined to be not listening to audio or not wearing the earpiece 2, to store energy for a next active period when the user is wearing the earpiece 2, for example. As another example, with the energy harvesting component 30, less energy may be needed from the media player 13 in the wired environment example when the earpieces 2 are wiredly connected to the media player 13. In addition, with the energy harvesting component 30, the sensors may be active in longer sequences with the same amount of battery usage.

In addition, in an example where the earpieces 2 are wirelessly connected to the media player 13, and no cable is needed, the user may have increased flexibility relative the media player 13. However, in such an example, the earpieces 2 may require a separate battery to drive the respective speaker elements and the first motion sensor 25 and pulse rate detector. Thus, in an example, the pulse rate detector may be controlled to be active for select periods and inactive for periods, so as to save energy even while the user is using the earphones to listen to audio or when the user is not using the earphones. Thereby, less energy may be needed compared to when continuously measuring the pulse rate. The pulse rate detector may be the most energy consuming component of the earpieces 2, and thus, it may be desirable to reduce energy consumption of the pulse rate detector. The pulse rate detector may be controlled, e.g., by the controller 120, to have inactive periods lasting for between 1 second and 10 minutes. In some examples the inactive periods lasts for five seconds, ten seconds, 30 seconds, 1 minute, 5 minutes or at any other period of time depending on embodiment. Further, the active period for measuring the pulse may be controlled, e.g., by the controller 120, to be between 1 second to 1 minute. In some examples the active periods lasts for one second, three seconds, ten seconds, 30 seconds, 45 seconds, or any other active period of time that may provide sufficient data. Thus, in this example, energy may be saved and thus the battery of the earpiece 2 and/or the battery of the example media player 13 may last longer.

The first motion sensor 25 (and/or the second motion sensor) may also be controlled, e.g., by the controller 120, to be inactive for select periods of time. The inactive periods of the motion sensor 25 may last for between 5 second and 5 minutes, for example. In an example, the inactive periods may last for five seconds, ten seconds, 30 seconds, or 1 minute. Correspondingly, the controller 120 may control the active periods of the first motion sensor 25 to last for between 5 second and 5 minutes, for example. In some examples the active periods lasts for five seconds, ten seconds, 30 seconds, or 1 minute.

In one example, the first motion sensor 25 (and/or the second motion sensor) in the earpieces 2 may be further used for handling manual commands of a user. For example, the controller 120 may monitor the motion sensor, for example, for indications of input commands and be configured to selectively control the audio output when the first motion sensor 25 of an earpiece 2 detects such a tap or touch command on the earpiece 2, the controller 120 may determine what the input tap or touch is a command intended to control the audio output, such as controls to pause/play through a single tap, to change a song, playlist, or genre through a double tap, and to activate a voice control through a triple tap, etc., only examples. In an example, the state determining activity/operations of the controller 120 may be momentarily disabled for a period of time when a manual tap action is detected, so as to not incorporate sensed motion data corresponding to the tap into the determination of the state of the user.

Moreover, the earphone system may include the microphone 35, e.g., in one or both earpieces 2 and/or the remote control unit 12, so that the earphone system may be used to record a sound from the user, e.g., for handling a phone call or voice commands for a connected media player 13, such as where the media player 13 is a smart phone. Moreover, the microphone 35 may be used to further increase the reliability of the detected state of the user. For example, if the user state is determined by the controller 120 to be a running state (i.e., based on the respective sensor data), the microphone may further be used for confirming that captured environmental sounds correlate to predetermined sounds associated with running. In another example, if the user state is determined by the controller 120 to be a sleeping state (i.e., based on the respective sensor data), captured sound by the microphone may be used for confirming that the captured environmental sounds correlate to predetermined sounds associated with sleeping. In still further examples, it the controller 120 may control the microphone to capture ambient sounds and based on that the captured ambient sounds the controller 120 may control the volume of the audio output to be increased. For example, in a determined noisy environment the volume may be adjusted to be higher than in a determined silent environment. The microphone 35 may alternatively or additionally be configured with in the media player 13, and the controller 120 may consider all captured ambient audio when determining the activity of the user.

Moreover, the controller 120 or the remote control unit 12 may include a user selectable physical on/off switch for enabling or disabling operations of the controller 120, for example, in controlling the audio output based on the user's detected state, e.g., selectively controlling whether operations of FIG. 7 are implemented. Accordingly, the user can prevent the audio output from being changed through user control of the controller 120 when the user changes activity by turning the on/off switch off, if the user so desires. In other embodiments, the on/off switch may be implemented as a user interface of an application on the media player 13, a user interface of the controller 120, of the remote control unit 12, or of another device in communication with the controller 120 or remote control unit 12, for example. As still another example, the example on/off switch may be a touch sensitive switch for a touch interface of the earpiece 2.

In an example, one or more or all operations described above may be implemented by one or more processors configured in the earpiece 2, the remote control unit 12, or the media player 13 such as through by a computer readable code stored on/in one or more non-transitory computer readable media of the example earpiece 2, remote control unit 12, or media player 13, that when executed by the one or more processors, cause the one or more processors to perform the one or more or all such operations. For example, the non-transitory computer readable media may store computer readable code to cause a controller to adjust the audio output from a media player 13 to earphones according to one or more or all embodiments described above. The non-transitory computer readable media may store computer readable code to cause the example one or more processors to detect a state of a user through sensor data from two different types of sensors, to detect corresponding movements of the user by control one or more motion sensors, to detect a pulse rate of the user through sensor data from one or more bio-signal sensors, such as one or more pulse rate detectors, and to control the one or more bio-signal sensors, and/or to control a transmitting of such respective sensor data from the one or more motion sensors and the one or more bio-signal sensors to the one or more processors. Further the non-transitory computer readable media may store computer readable code to control a selecting or an adjusting of a providing to, or receipt of, audio output, e.g., from such a media player 13, output through a speaker of the earphones, e.g., based on the determined state of the user.

The earphones 1, earpieces 2, media player 13, remote control unit 12, first motion sensor(s) 25, second motion sensor(s), pulse rate detector(s), IR led 26, IR sensor 27, speaker 24, accelerometers, controller 120, I²C circuit 121, MCU, BLE circuit 122, control buttons 123, power control 28, energy harvesting component 30, energy storage 31, boost converter 32, microphone 35, phone connection 33, communication module, and remote server, as only examples, described with respect to FIGS. 1-8 and that perform the operations described in this application are implemented by hardware components configured to perform the operations described in this application that are performed by the hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 1-8 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that are performed by the hardware components and the methods as described above. In one example, the instructions or software include machine code that is directly executed by the one or more processors or computers, such as machine code produced by a compiler. In another example, the instructions or software includes higher-level code that is executed by the one or more processors or computer using an interpreter. The instructions or software may be written using any programming language based on the block diagrams and the flow charts illustrated in the drawings and the corresponding descriptions in the specification, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An earphone system, comprising:
   an earpiece configured with an arrangement within an outer ear of a user's ear for listening to audio from a speaker, the earpiece including the speaker and an optical sensor within the arrangement of the earpiece within the outer ear;
   a motion sensor configured to detect motion of the user; and
   one or more processors configured to
   determine an activity state of the user based on a combined consideration of obtained optical sensor data from the optical sensor and obtained motion data from the motion sensor, and
   control a user sensory output to the user based on the determined activity state of the user.

2. The earphone system of claim 1, wherein, for the determining of the activity state of the user, the one or more processors are configured to determine a preliminary activity state of the user based on the optical sensor data from the optical sensor, and confirm the preliminary activity state based on the motion data from the motion sensor, to determine the activity state of the user.

3. The earphone system of claim 2, wherein, for the determining of the activity state of the user, the one or more processors are configured to determine the activity state of the user based on learned activity states of the user over time.

4. The earphone system of claim 1, wherein the determined activity state of the user is a learned activity state.

5. The earphone system of claim 4,
   wherein the one or more processors are configured within the earpiece, and
   wherein the motion sensor is configured in the earpiece, another earpiece of the earphone system, or a media device of the earphone system separate from respective one or more earpieces of the earphone system.

6. The earphone system of claim 5,
   wherein the sensory output is output audio, and
   wherein the one or more processors are configured to control output of the output audio dependent on the determined activity state of the user, including control of an adjustment of the output audio to match a determined low activity when the determined activity state is a predetermined low activity state and an adjustment of the output audio to match a determined high activity when the determined activity state is a predetermined high activity state.

7. The earphone system of claim 4, wherein the one or more processors are configured in a media device of the earphone system separate from respective one or more earpieces of the earphone system.

8. The earphone system of claim 7, wherein the motion sensor is configured in the media device.

9. The earphone system of claim 8,
   wherein, for the control of the user sensory output, the one or more other processors further control an adjustment of audio media output to the user, as the user sensory data, to match a determined low activity when the determined activity state is a predetermined low activity state and an adjustment of the audio media output to the user to match a determined high activity when the determined activity state is a predetermined high activity state.

10. The earphone system of claim 1, wherein
    the motion sensor and the one or more processors are configured in a media device of the earphone system separate from respective one or more earpieces of the earphone system,
    the media device includes a user interface, and
    the control of the user sensory output to the user based on the determined activity state is dependent on which exercise activity state, among plural exercise activity states, is determined to be the activity state.

11. The earphone system of claim 1, wherein, when the motion data from the motion sensor and the optical sensor data from the optical sensor indicate the user is resting, the one or more processors determine whether the activity state is a sleeping state trained based on detected movements over time by the motion sensor that are below a predetermined threshold, the trained sleeping state being updated over time.

12. The earphone system of claim 1, wherein the one or more processors determine where the motion data from the motion sensor and the optical sensor data from the optical sensor falls on a determined sleep-to-workout scale based on detected changes in movements of the user, to determine the activity state of the user.

13. The earphone system of claim 1, wherein the one or more processors are configured to
    determine between plural associated sub-states of the determined activity state based on detected changes in heart rate within a range of heart rates indicated by bio-signal data of a bio-sensor and corresponding to the determined activity state, where the optical sensor is the bio-signal sensor, and
    selectively control the user sensory output based on the determination between the plural sub-states.

14. The earphone system of claim 13, wherein, when the determined activity state is a workout state, the plural associated sub-states include two or more of warming up, running, lifting weights, bicycling, climbing, dancing, jumping, doing yoga, and stretching sub-states.

15. The earphone system of claim 13, wherein the one or more processors consider between the plural associated sub-states of the determined activity state based on location information regarding a location of the user.

16. The earphone system of claim 15, wherein the one or more processors are configured within the earpiece and the one or more processors determine the location of the user.

17. The earphone system of claim 16, wherein the one or more processors are configured within a media device of the earphone system and separate from respective one or more earpieces of the earphone system, and the one or more processors determine the location of the user.

18. The earphone system of claim 13, wherein the determination between the plural sub-states is based on a determined progression between the plural sub-states.

19. The earphone system of claim 1, further comprising a remote control unit, separate from respective one or more earpieces of the earphone system, comprising another motion sensor and a user control interface for user selective further control of the user sensory output,
wherein the motion sensor is configured in the earpiece, and
wherein the determining of the activity state further considers other obtained motion data from the other motion sensor.

20. The earphone system of claim 1, wherein the earpiece further comprises a communication module and wirelessly connects with a media device to receive audio output, corresponding to the user sensory output, using the communication module.

21. The system of claim 20, wherein the system further comprises another earpiece, wherein the earpiece and the other earpiece are wiredly connected.

22. The earphone system of claim 1, wherein the one or more processors are further configured to filter the optical sensor data from the optical sensor using the motion data from the motion sensor, included in the earpiece, and/or motion data from another motion sensor of the earphone system.

23. The earphone system of claim 1, wherein the one or more processors are further configured to monitor the motion data of the motion sensor, included in the earpiece, and/or other motion data from another motion sensor of the earphone system for detected indications that the user is inputting a touch or tap command, and to not rely on, for the determining of the activity state of the user, the motion data of the motion sensor and/or the other motion data of the other motion sensor that are determined to correspond to the detected indications that the user is inputting the touch or tap command.

24. The earphone system of claim 23, wherein the one or more processors are configured to determine whether the touch or tap is a command
to control, with respect to the user sensory output, a pausing or resuming of audio output,
to control a change in a song, genre, or playlist in the audio output, or
to control an activation of a voice control.

25. The earphone system of claim 1, further comprising a remote control unit, separate from respective one or more earpieces of the earphone system, including the one or more processors and a user control interface for user selective further control of the user sensory output,
wherein the respective one or more earpieces are wiredly connected.

26. The earphone system of claim 1, wherein the one or more processors are further configured to obtain cadence sensor data, and to determine the activity state further based on the obtained cadence sensor data.

27. The earphone system of claim 1, wherein, for the determining of the activity state of the user, the one or more processors are configured to determine the activity state of the user based on one or more user set activity states of the user with respect to user select optical sensor data and motion data.

28. The earphone system of claim 1, wherein the one or more processors are further configured to determine the activity state from among plural user preset activity states set through a user interface of the earphone system.

29. The earphone system of claim 1,
wherein the one or more processors include plural processors and the system further comprises a microphone and another motion sensor, and
wherein at least one processor of the plural processors is configured to determine a preliminary activity state of the user using the other motion sensor, determine an activity state related to the preliminary activity state and represented by ambient sounds captured by the microphone, and control provision of information to the user based on the activity state represented by the captured ambient sounds.

30. The earphone system of claim 29, wherein the determination of the preliminary activity state of the user is based on learned activity states of the user over time.

31. The earphone system of claim 1, wherein the system further comprises a microphone and another motion sensor, and
wherein at least one processor of the one or more processors is configured to detect a learned activity state of the user dependent on the other motion sensor and ambient sounds captured by the microphone, and control provision of information to the user based on the detected learned activity state.

32. An earphone method of a system having a motion sensor and an earpiece configured with an arrangement within an outer ear of a user's ear for listening to audio from a speaker, the earpiece including the speaker and an optical sensor within the arrangement of the earpiece within the outer ear, the method comprising:
controlling respective measuring of bio-signals and motion changes of a user by the earpiece;
determining a learned activity state of the user based on a combined consideration of obtained bio-signal data from the bio-sensor and obtained motion data from the motion sensor; and
controlling a provision of user sensory output to the user based on the determined activity state.

33. An earphone system, comprising:
an earpiece configured with an arrangement within an outer ear of a user's ear for listening to audio from a speaker, the earpiece including an accelerometer, and both of an optical sensor and the speaker within the arrangement of the earpiece within the outer ear; and
one or more processors configured to
determine an activity state transition of the user based on a combined consideration of obtained optical sensor data from the optical sensor and obtained motion data from the accelerometer, and control a provision of audio information from a media player to the earpiece, for the listening to the audio, based on the determined activity state transition of the user.

34. The earphone system of claim 33, further comprising the media player,
wherein the media player comprises at least one of the one or more processors and the earpiece is configured for wireless communication with the media player.

35. The earphone system of claim 34, wherein the media player controls the provision of the audio information to the earpiece.

36. The earphone system of claim 33, wherein the system further comprises another earpiece, wherein the earpiece and the other earpiece are wiredly connected.

* * * * *